United States Patent
Wilhelm et al.

(10) Patent No.: US 8,381,571 B2
(45) Date of Patent: Feb. 26, 2013

(54) METHOD AND APPARATUS FOR ASSESSING THE PENETRATION OF TOOTH CLEANING ELEMENTS IN THE GINGIVAL POCKET

(75) Inventors: Joachim Wilhelm, Frankfurt (DE); Günter Helbig, Schwalbach (DE); Bernd Trebitz, Butzbach (DE)

(73) Assignee: Braun GmbH, Kronberg (DE)

( * ) Notice: Subject to any disclaimer, the term of this patent is extended or adjusted under 35 U.S.C. 154(b) by 348 days.

(21) Appl. No.: 12/817,292

(22) Filed: Jun. 17, 2010

(65) Prior Publication Data

US 2011/0313825 A1   Dec. 22, 2011

(51) Int. Cl.
*G01N 3/56* (2006.01)
*G01N 19/02* (2006.01)
*G01N 19/00* (2006.01)

(52) U.S. Cl. ............... 73/7; 73/865.9; 382/128
(58) Field of Classification Search .......... 73/7
See application file for complete search history.

(56) References Cited

U.S. PATENT DOCUMENTS

| | | | |
|---|---|---|---|
| 5,120,229 A * | 6/1992 | Moore et al. | 434/263 |
| 6,524,105 B2 * | 2/2003 | Raffeiner | 433/213 |
| 6,969,258 B1 * | 11/2005 | Shaygan | 434/263 |
| 2010/0280793 A1 * | 11/2010 | Wilhelm et al. | 702/182 |
| 2012/0122065 A1 * | 5/2012 | Snoad | 434/263 |

FOREIGN PATENT DOCUMENTS

JP     2012029755 A   *  2/2012

OTHER PUBLICATIONS

"Development and laboratory evaluation of a new toothbrush with a novel brush head design", Donna Beals et al., American Journal of Dentistry, vol. 13, Special Issue, Mar. 2000.

* cited by examiner

*Primary Examiner* — Peter Macchiarolo
*Assistant Examiner* — Natalie Huls
(74) *Attorney, Agent, or Firm* — David M. Weirich

(57) ABSTRACT

A method and apparatus for assessing the penetration of tooth cleaning elements into a simulated gingival pocket. In one embodiment, the apparatus includes a tooth shaped member, wherein at least a portion of the tooth is transparent to light; a gum member positioned on a first side of the tooth shaped member; a simulated gingival pocket created between the gum member and the tooth shaped member; and an imaging device configured to obtain a plurality of images related to the gingival pocket, and bristle penetration into the gingival pocket.

21 Claims, 5 Drawing Sheets

METHOD AND APPARATUS FOR ASSESSING THE PENETRATION OF TOOTH CLEANING ELEMENTS IN THE GINGIVAL POCKET

FIELD OF THE INVENTION

This invention relates to a method and apparatus for assessing the penetration of tooth cleaning elements into the gingival pocket. This invention finds a particularly useful application in assessing the performance of toothbrushes.

BACKGROUND OF THE INVENTION

Toothbrushes typically have a head with a plurality of tooth cleaning elements, such as for example bristle filaments and elastomeric elements, attached to the head for cleaning teeth, removing bacterial plaque, and stimulating gums. It is desirable to have a toothbrush with cleaning elements that penetrate into the gingival pocket between the gums and the teeth to remove plaque that builds up below the gum line.

SUMMARY OF THE INVENTION

An apparatus for assessing the penetration of tooth cleaning elements into the gingival pocket is provided herein. In one embodiment, the apparatus includes a tooth shaped member; a gum member positioned on a first side of the tooth shaped member; a simulated gingival pocket created between the gum member and the tooth shaped member; and an imaging device configured to obtain a plurality of images related to the gingival pocket, for example bristle penetration into the gingival pocket.

In addition, a method of assessing the penetration of cleaning elements into the gingival pocket is provided herein. One embodiment includes: obtaining data from one or more reference images of at least a portion of a gingival pocket through at least a portion of a transparent tooth; obtaining data from a plurality of sample images through at least a portion of the transparent tooth while brushing the tooth with a toothbrush; comparing data from the plurality of sample images to data from the one or more reference images; and determining the penetration depth of at least one cleaning element into the gingival pocket as a function of the comparison.

Another embodiment of a method of assessing the penetration of cleaning elements into the gingival pocket includes providing a dentition having a simulated tooth and a simulated gum forming a simulated gingival pocket between the simulated tooth and the simulated gum; providing an imaging sensor for obtaining one or more reference images when no brushing activity is being conducted on the dentition and one or more sample images during brushing activity with a toothbrush having a plurality of cleaning elements; and determining a penetration depth of at least one cleaning element within the simulated gingival pocket as a function of comparing data from one or more sample images to data from one or more reference images.

In yet another embodiment, a method is provided of comparing two toothbrushes to determine which toothbrush has greater cleaning element penetration into a gingival pocket. The method includes providing a dentition device having a simulated tooth and a simulated gum forming a simulated gingival pocket therebetween. In addition an image detector for capturing data is provided. The dentition is brushed with a first toothbrush and the image detector captures first toothbrush data related to the first toothbrush cleaning element penetration into the simulated gingival pocket. The detention is brushed with a second toothbrush and the image detector captures second toothbrush data related to the second toothbrush cleaning element penetration into the simulated gingival pocket. Finally a determination is made of which one of the first and second toothbrush has greater cleaning element penetration into the gingival pocket as a function of the first toothbrush data and the second toothbrush data.

Other features and advantages of the invention will be apparent from the description and drawings, and from the claims.

DETAILED DESCRIPTION OF THE DRAWINGS

FIG. 2 is the apparatus of FIG. 1 having a light source turned on;

DETAILED DESCRIPTION OF THE INVENTION

Toothbrushes often have a plurality of tooth cleaning elements secured to the head of the toothbrush. These tooth cleaning elements may include, for example, bristles, elastomeric elements, pivotal elements or any other cleaning element. The plurality of tooth cleaning elements on a toothbrush may include a single type of tooth cleaning element or combinations of different types of tooth cleaning elements. Furthermore, a particular type of tooth cleaning element may have several different forms and/or properties, such as for example, different thickness, stiffness, mounting angle, length and composition. In addition, the tooth cleaning elements may be grouped into a wide variety of configurations, such as for example bristle tufts, elongated bristle tufts, angled bristle tufts, sets of elastomeric fins, or elastomeric elements with a variety of different sizes and shapes of wiping edges. The embodiments described herein for illustration refer to bristles, however, the present invention is applicable for assessing the penetration of other tooth cleaning elements in the gingival pocket, without any limitations on the material or dimensions.

Figure 1:
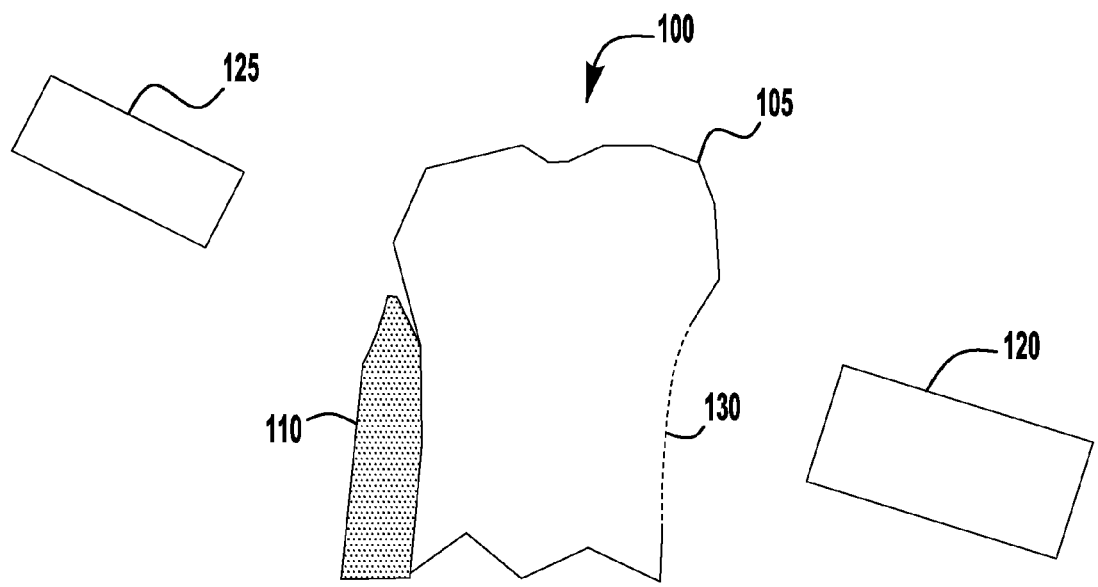
FIG. 1 is an exemplary elevational view of an apparatus for assessing the level of penetration of bristles into a gingival pocket.

FIG. 1 illustrates an embodiment of an apparatus 100 for assessing the penetration of bristles into a gingival pocket. The apparatus 100 includes a tooth shaped member 105, a gum member 110, an imaging sensor 120 and a light source 125. In one embodiment, gum member 110 is made up of a resilient material. In one embodiment, the gum member 110 has a composition and shape which approximates the reaction of human gum tissue to a brushing operation. Such reaction characteristics may depend for example on the age of the user, the health of the user's gums, and the like. Such characteristics may be reduced to average values for the intended users of the toothbrush(es) being tested, and then an appropriate gum member 110 chosen to exhibit those characteristics. The gum member 110 may be composed of, in some embodiments, polyvinyl, silicon, soft rubber materials, or combinations thereof. Other simulated gum materials may also be used.

Light source 125 may be a single light source, but may be multiple light sources, such as for example a plurality of fiber optic lights that may be located at different orientations so as to provide desired light levels. A simulated gingival pocket 115 is formed between gum member 110 and tooth shaped member 105. In certain embodiments, at least a portion of tooth shaped member 105 is transparent so that an image of the gingival pocket may be obtained through at least a portion of tooth shaped member 105. In addition, a transparent tooth shaped member 105 allows light to enter the gingival pocket which permits the image sensor 120 to obtain quality images. In one embodiment, the entire tooth shaped member 105 is substantially transparent. In one embodiment tooth shaped member 105 is made of glass. In yet another embodiment, tooth shaped member 105 is translucent allowing some light to pass through to obtain an image of the gingival pocket. In addition, optionally tooth shaped member 105 is hollow and includes a cutout portion 130. Cutout portion 130 may be disposed between the gum member 110 and the image sensor 120, on the opposite side of the tooth shaped member 105 from the gum member 110, and is preferably large enough not to interfere with the focusing of image sensor 120 on the gingival pocket 115. Image sensor 120 may be a two dimensional photodetector array, a high speed camera, high speed video camera or any other imaging device.

Figure 2:
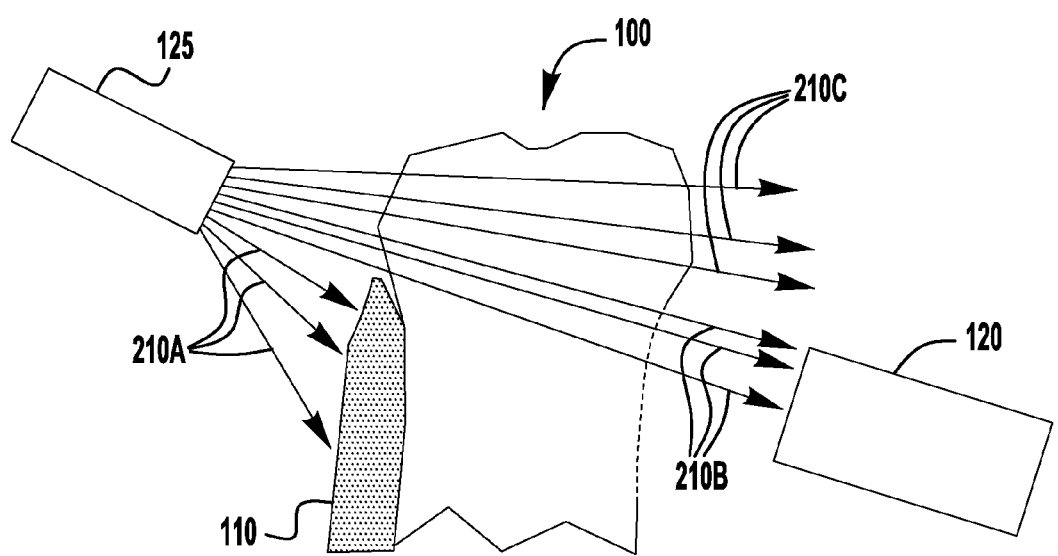
Figure 3:
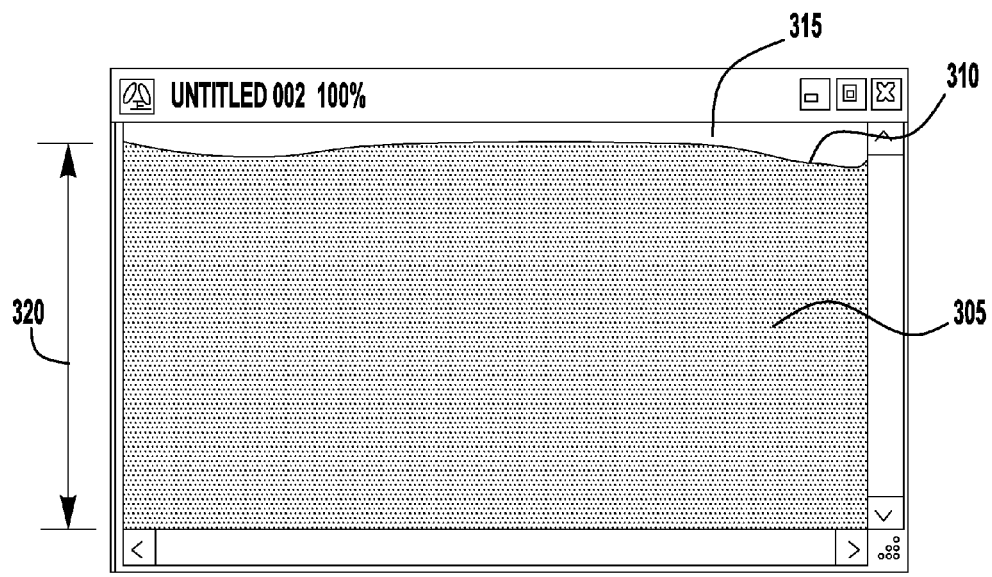
FIG. 3 is an exemplary view of a reference image showing a gum line.

FIG. 2 is the apparatus 100 with light 125 turned on. Light beams 210A, 210B, 210C are emitted from light 125. Gum member 110 may be opaque and accordingly light beams 210A impinging on the gum member 110 do not pass through gum member 110. Light beams 210B and 210C pass through tooth shaped member 105, which may be transparent. Light beams 210C pass over image sensor 120, and light beams 210B strike image sensor 120. Accordingly, image sensor 120 captures a reference image 300 as shown in FIG. 3 having two portions. A dark portion 305 is where the light beams 210A were stopped by the gum member 110. A light portion 315 is where the light beams 210B pass above the gum member 110, through the tooth-shaped member 105, finally to be detected by the image sensor 120. Therefore, the border between the dark portion 305 and the light portion 315 represents the gum line 310 of the apparatus 100.

Reference image 300 is taken during a period of time when no brushing activity is taking place. Reference image 300 is shown in black and white; however, in actual practice reference image 300 may be a color image or a grayscale image that is preferably converted to a black and white image. A picture-analysis-software may be used to analyze reference image 300, such as for example, IMAGE-PRO, available through Media Cybernetics Inc. In one embodiment, the picture-analysis-software measures a distance 320 from the bottom of the image 300 to the gum line 310 at several incremental positions along the horizontal axis. Each distance 320 and incremental position along the horizontal axis may be stored in memory for comparison to the sample images (discussed in detail below).

In one embodiment, the position of the gum member 110 with respect to the image sensor 120 is fixed. Accordingly, it is not necessary to image the gum line 310 each time a new toothbrush is tested. Rather, the picture-analysis-software may simply retrieve the prior gum line 310 from memory.

Still yet, in one embodiment, the gum line is may be represented by an equation, and the equation may be manually input into the picture-analysis-software. In another embodiment, the gum line is manually drawn and input into the picture-analysis-software.

Figure 4:
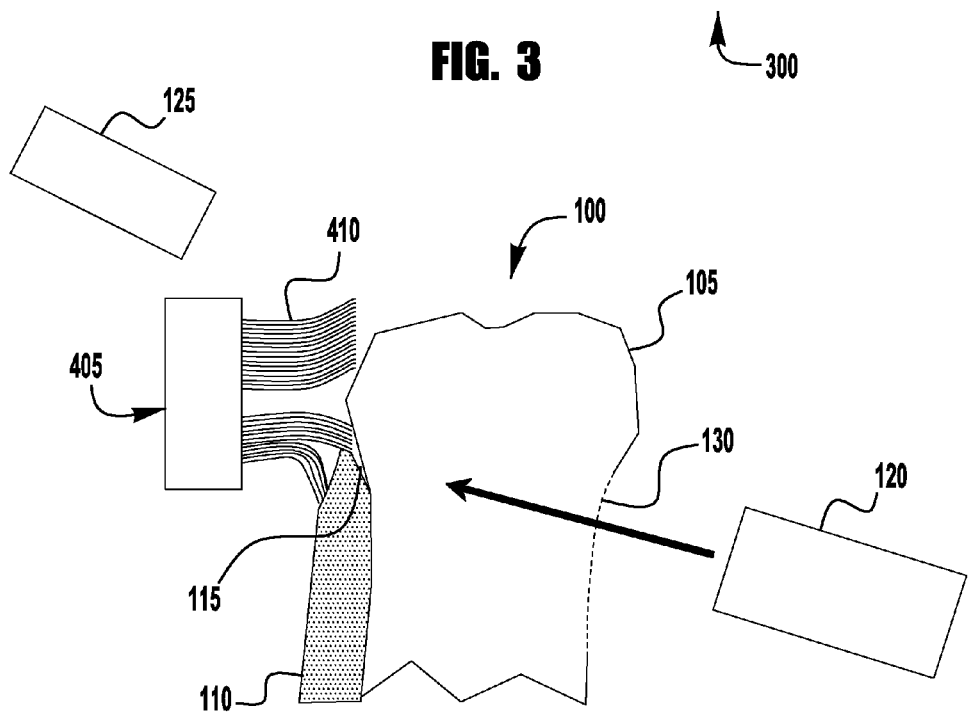
FIG. 4 is the apparatus of FIG. 1 during brushing activity with a toothbrush.

FIG. 4 illustrates the apparatus 100 of FIG. 1 during a brushing activity. Toothbrush 405 is moved in a brushing action along apparatus 100, which includes tooth shaped member 105 and gum member 110. Toothbrush 400 may be retained by a mechanical arm and moved mechanically wherein the brushing motion and brushing pressure may be accurately controlled thereby creating a repeatable testing assessment. As toothbrush 405 is moved in a brushing motion, some of bristles 410 penetrate into gingival pocket 115. Light source 125 (which may be several light sources positioned at various locations) is illuminated and image sensor 120 captures sample images during the brushing motion. In one embodiment, image sensor 120 captures over eighty sample images 500 (FIG. 5) per cycle. A cycle is the movement of the toothbrush away from and back to its original position. Accordingly, image sensor 120 is preferably a high speed camera or high speed video recorder. Image sensor 120 captures sample images of the toothbrush bristles 410 penetrating into the gingival pocket 115. Picture-analysis-software may be used to analyze the bristle penetration depth into the gingival pocket.

Figure 5A:
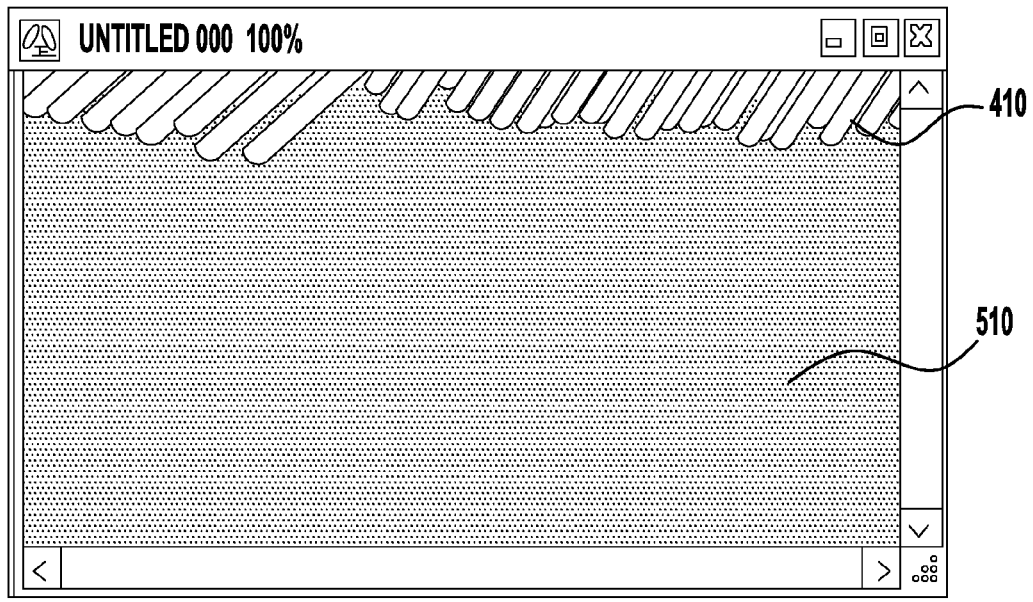
FIG. 5A is an exemplary sample image of bristles penetrating into the gingival pocket before processing.
Figure 5B:
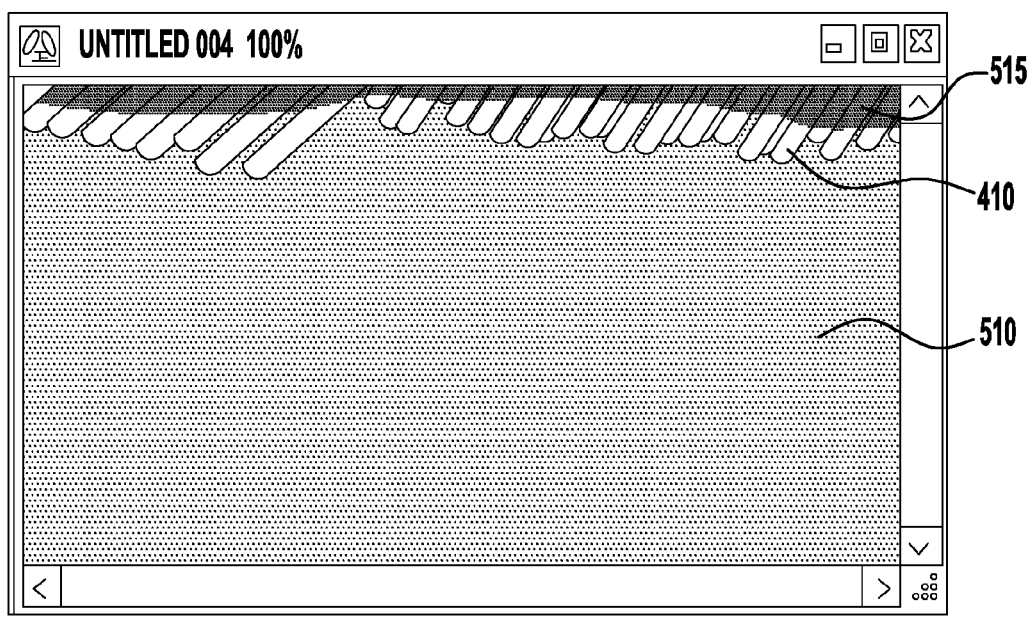
FIG. 5B is the exemplary sample image of FIG. 5A masked with the gum line of FIG. 3.

FIG. 5A illustrates a sample image 500 taken during brushing activity. In one embodiment, the brushing activity is stopped, or paused, and an image is taken while toothbrush 405 is stationary. In some embodiments, a plurality of sample images 500 are taken during the brushing activity. Sample image 500 includes bristles 410 and a dark portion 510 that corresponds to a portion of gum member 110. In one embodiment, such native images 500 may be used without further processing to assess the performance of the toothbrush 405 and its bristles 410. In another embodiment, the native images 500 may be further processed before the brushing performance evaluation. For example, the picture-analysis-software can apply a mask 515 to sample image 500 creating image 502, which is illustrated in FIG. 5B. Mask 515 may be obtained from data contained in reference image 300 to reflect the gum line 310 shown in FIG. 3. In that way a quantitative assessment may be made regarding the depth of bristle 410 penetration below the gum line mask 515 at each of the incremental positions along the horizontal axis.

Figure 6:
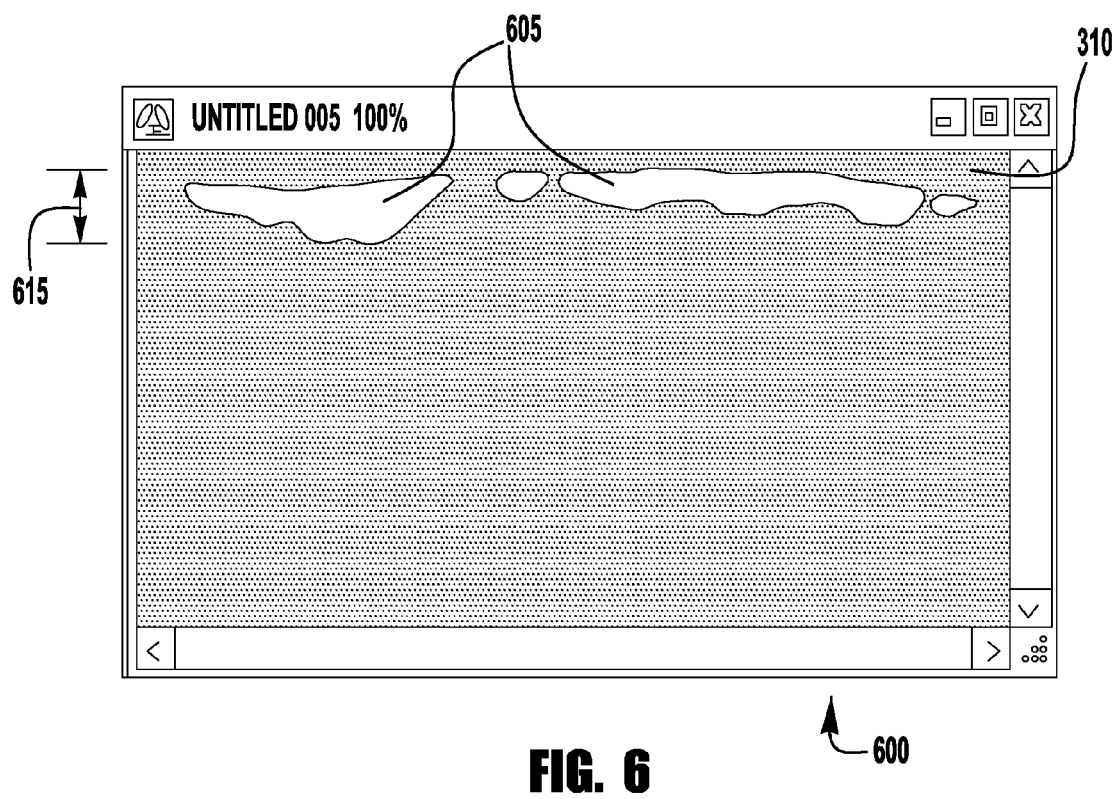
FIG. 6 is an exemplary embodiment of the sample image of FIG. 5A combined with the reference image of FIG. 3 illustrating bristle penetration depth, with pixel values set to black or white.

For example, as shown in FIG. 6, the picture-analysis-software may convert image 502 to a black and white image 600. The white portion 605 of black and white image 600 illustrates the depth of penetration of the bristles 410 below the gum line 310 into the gingival pocket 115. The picture-analysis-software calculates the depth 615 of the white area 605 for several incremental positions along the horizontal axis. The depth may be calculated by measuring the depth of the white area 605 or by measuring a distance from the bottom of the frame to the bottom of the white area 605 and subtracting that distance from the distance from the bottom of the frame to the gum line 310 (which was previously calculated and saved in memory). The picture-analysis-software may provide an output which is a value identifying the maximum depth of penetration, a value for each incremental position along the horizontal axis, a value identifying the average bristle penetration depth, or any other statistical value related to bristle penetration.

The picture analysis software may analyze the entire image or a subset of the image to obtain data used to determine bristle 410 penetration into the gingival pocket 115. In one embodiment, bristle depth penetration is mathematically calculated from data derived from the reference image 300 and data derived from the sample image 500.

Figure 7:
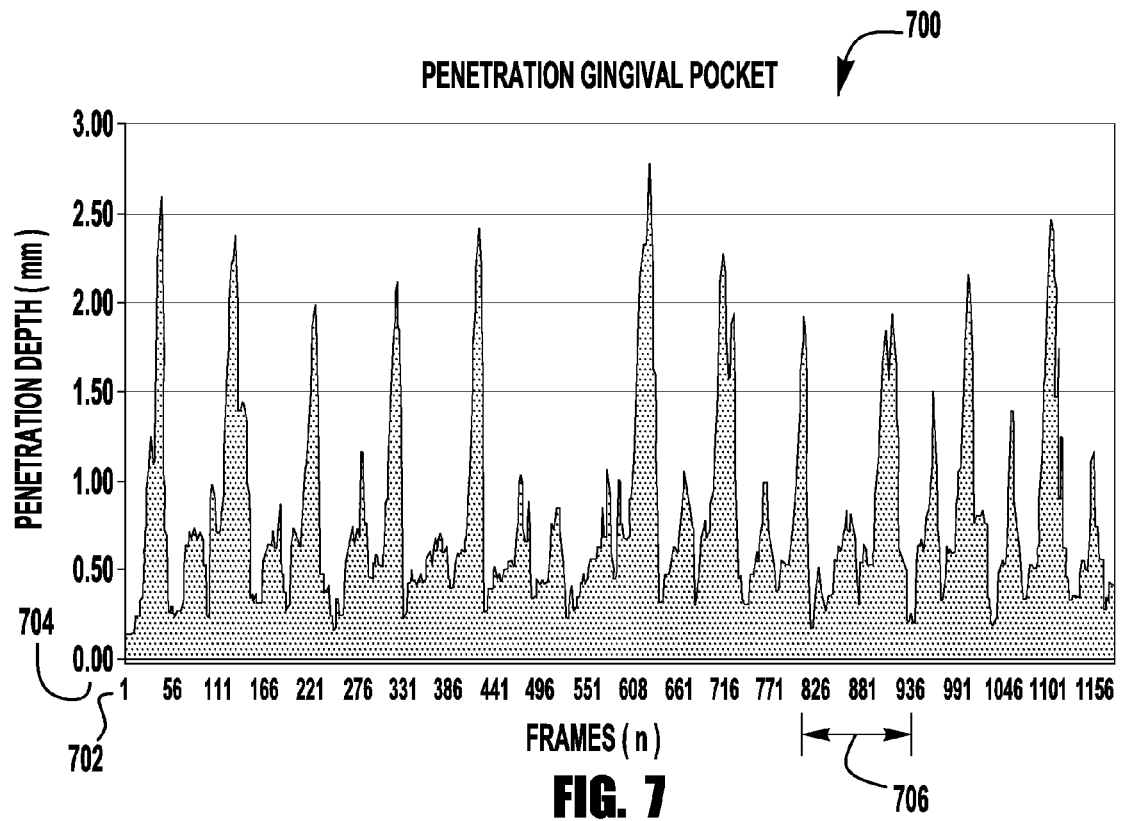
FIG. 7 is a graphical representation of the depth of the bristle penetration into the gingival pocket over a series of brush strokes based on data from derived from a number of sample images.

In one embodiment, picture-analysis-software provides a single value identifying the maximum depth of a bristle 410 penetration into the gingival pocket 115 for each sample image 500. That information may be imported to an application, such as for example, Microsoft EXCEL, and plotted in a graph. FIG. 7 illustrates one such graphical representation 700. Graphical representation 700 includes an x-axis 702 that identifies each sampled image 500 from which data was obtained to identify bristle penetration, numbered 1 through n=1156. The representation 700 also includes a y-axis 704 which identifies the maximum depth of bristle penetration in millimeters for bristle filaments from each sampled image 500. In graphical representation 700, sample images 500 were taken during 15 cycles of brush strokes of toothbrush 405. A cycle is the movement of the toothbrush away from a first position and back to that first position. For example, if the brush stroke is a linear back-and-forth motion, a cycle would be movement of the brush forward and back to its original position. One such cycle is shown at 706 in FIG. 7.

The general exemplary methods of ascertaining bristle penetration into the gingival pocket discussed above are useful in many different ways not specifically disclosed herein to identify toothbrushes that have desirable cleaning characteristics. In one potential variation, determining a single value which corresponds to the cleaning characteristics of the toothbrush may be calculated. Thus, a single average maximum depth of bristle penetration may be calculated by first determining the peak bristle penetration in each cycle of the brushing action, then adding each of those peak penetrations for each cycle together to generate a sum, and next dividing that sum by the total number of cycles. The resulting average is a single number representing the average maximum bristle penetration in each cycle.

Two different toothbrushes may be compared to determine which toothbrush has greater gingival pocket penetration. The comparison may be made by comparing recorded imaging data, comparing an average bristle depth penetration, comparing a maximum bristle depth penetration, comparing an average maximum bristle depth penetration over a set number of cycles, or any other statistical analysis of data derived from images captured during brushing with the toothbrush. Comparison of two different toothbrushes may be made for advertising purposes allowing one manufacture to make advertising claims that its toothbrush is superior to a competitor's toothbrush. The advertising claims may be made in any advertising media, such as for example, television or print. In addition, such advertising claims may be made on the toothbrush packaging.

Figure 8:
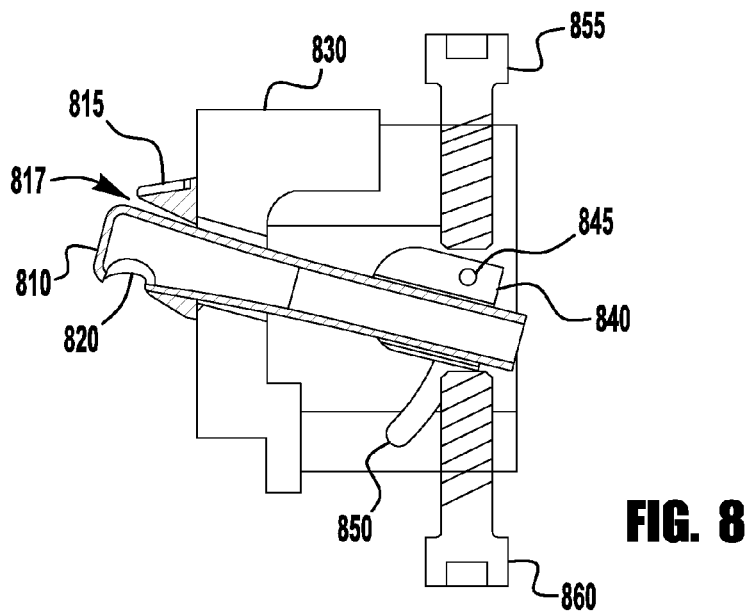
FIG. 8 is an exemplary dentition for assessing the level of penetration of bristles into the gingival pocket.

FIG. 8 shows an exemplary dentition 800 for assessing the level of penetration of bristles into the gingival pocket 817. Dentition 800 includes a tooth shaped member 810 and frame member 830. Tooth shaped member 810 is preferably made of glass and includes a cutout portion 820 permitting the capture of images through the side wall of tooth shaped member 810. Tooth shaped member 810 is held by clamp 840 which includes pin 845. Pin 845 rides in track guide 850 allowing tooth shaped member 810 to pivot. Screw pins 855 and 860 are screwed into frame 830 and contact clamp 840. Twisting screw pin 855 clockwise and screw pin 860 counterclockwise pivots the tooth shaped member 810 towards gum shaped member 815 thereby making gingival pocket 817 smaller. Conversely twisting screw pin 855 counterclockwise and pin 860 clockwise rotates the tooth shaped member 810 away from gum member 815 thereby making gingival pocket 817 larger. Accordingly, the methods of assessing penetration into gingival pockets may be conducted on any number of different sized gingival pockets.

While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. For example, providing a plurality of different shapes of simulated teeth representing different types of teeth, such as molars or eye teeth, is contemplated herein. Therefore, the invention in its broader aspects is not limited to the specific details, representative apparatus and methods, and illustrative examples shown and described. Accordingly, departures may be made from such details without departing from the spirit or scope of the applicant's general inventive concept.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for assessing the penetration of one or more bristles into a gingival pocket, the apparatus comprising:
    a tooth shaped member, at least a portion of which is translucent or transparent;
    a gum member positioned on at least one side of the tooth shaped member;
    a simulated gingival pocket between the gum member and the tooth shaped member; and
    an imaging device configured to obtain data related to tooth cleaning element penetration into the gingival pocket, wherein the tooth shaped member contains a cut out on a side of the tooth shaped member opposite from the gum member.

2. The apparatus of claim 1 wherein the imaging device is further configured to obtain data related to the gingival pocket.

3. The apparatus of claim 1 wherein the imaging device is configured to obtain data related to bristle penetration into the gingival pocket during brushing with a toothbrush.

4. The apparatus of claim 1 further comprising a light source positioned to shine light into the gingival pocket.

5. The apparatus of claim 1 wherein at least one of the tooth shaped member and the gum member is moveable to change the size of the gingival pocket.

6. The apparatus of claim 1 further comprising analytical software on a computer readable medium for comparing data related to one or more sample images to data related to one or more reference images.

7. A method of assessing penetration of tooth cleaning elements into a gingival pocket, the method comprising:
providing a dentition having a transparent tooth shaped member;
obtaining reference image data for a gum line of the gingival pocket;
providing an image sensor for obtaining at least one sample image of the gingival pocket through at least a portion of the transparent tooth shaped member, while brushing the tooth shaped member with a tooth brush;
comparing data obtained from the at least one sample image to data obtained from the at least one reference image; and
determining a penetration depth of at least one tooth cleaning element into the gingival pocket as a function of the comparison of data from the at least one sample image to the reference image data.

8. The method of claim 7 further comprising determining a maximum penetration depth of the tooth cleaning elements into the gingival pocket.

9. The method of claim 7 further comprising determining a penetration depth of the cleaning elements into the gingival pocket for a first toothbrush and determining a penetration depth of the tooth cleaning elements into the gingival pocket for a second toothbrush.

10. The method of claim 7 wherein the brushing activity is paused while obtaining the sample image.

11. A method of assessing penetration of toothbrush cleaning element into a gingival pocket, the method comprising:
providing a dentition having a tooth shaped member and a simulated gum forming a simulated gingival pocket between the tooth shaped member and the simulated gum;
obtaining one or more reference images of a simulated gum line;
providing an imaging sensor for obtaining one or more sample images during brushing activity with a first toothbrush; and
determining penetration depth of at least one cleaning filament within the simulated gingival pocket as a function of comparing data from the one or more sample images to data from the one or more reference images.

12. The method of claim 11 further comprising providing a light source to shine light into the simulated gingival pocket.

13. The method of claim 11 wherein obtaining one or more reference images of a simulated gum line comprises providing an imaging sensor for obtaining one or more reference images when no brushing activity is taking place.

14. The method of claim 11 wherein obtaining one or more reference images of a simulated gum line comprises retrieving the one or more reference images from memory.

15. The method of claim 11 wherein the brushing activity is paused while obtaining the one or more sample images.

16. The method of claim 11 wherein the tooth shaped member is translucent or transparent.

17. The method of claim 11 further comprising providing a hollow tooth shaped member with a cut out portion configured to allow an image to be taken of the wall of the tooth opposite the cutout portion.

18. The method of claim 11 wherein a size of the simulated gingival pocket in the dentition is adjustable.

19. The method of claim 11 further including the steps of:
brushing the dentition with a second toothbrush and using the image sensor to capture second toothbrush data related to the second toothbrush bristle penetration into the simulated gingival pocket; and
determining whether one of the first and second toothbrushes has greater cleaning element penetration into the gingival pocket as a function of the first toothbrush data and the second toothbrush data.

20. The method of claim 19 further comprising making an advertising claim that one of the first and second toothbrush has greater cleaning element penetration into the gingival pocket.

21. The method of claim 20 wherein making the advertising claim includes one of placing an advertisement in a media and placing the advertisement claim on toothbrush packaging.

* * * * *